US00PP25170P3

(12) United States Plant Patent
Roe

(10) Patent No.: US PP25,170 P3
(45) Date of Patent: Dec. 16, 2014

(54) ***CITRUS RETICULATA* PLANT NAMED 'WG 02'**

(50) Latin Name: *Citrus reticulata*
Varietal Denomination: WG 02

(71) Applicant: Bill Roe, Eagle Lake, FL (US)

(72) Inventor: Bill Roe, Eagle Lake, FL (US)

(73) Assignee: GJH LLC, Winter Haven, FL (US)

( * ) Notice: Subject to any disclaimer, the term of this patent is extended or adjusted under 35 U.S.C. 154(b) by 97 days.

(21) Appl. No.: 13/815,379

(22) Filed: Feb. 25, 2013

(65) Prior Publication Data

US 2014/0245502 P1 Aug. 28, 2014

(51) Int. Cl.
*A01H 5/00* (2006.01)

(52) U.S. Cl.
USPC ..... Plt./202

(58) Field of Classification Search
USPC ..... Plt./202
See application file for complete search history.

*Primary Examiner* — Annette Para
(74) *Attorney, Agent, or Firm* — Cassandra Bright

(57) ABSTRACT

A new and distinct *Citrus reticulata* cultivar named 'WG 02' is disclosed, characterized by having distinctive fruit of typical oblate appearance that peels easily The fruit has a very low seed count and maintains moderately high acid levels. Additionally, the new variety produces fruit that is harvested in November through December.

2 Drawing Sheets

Figure 1:
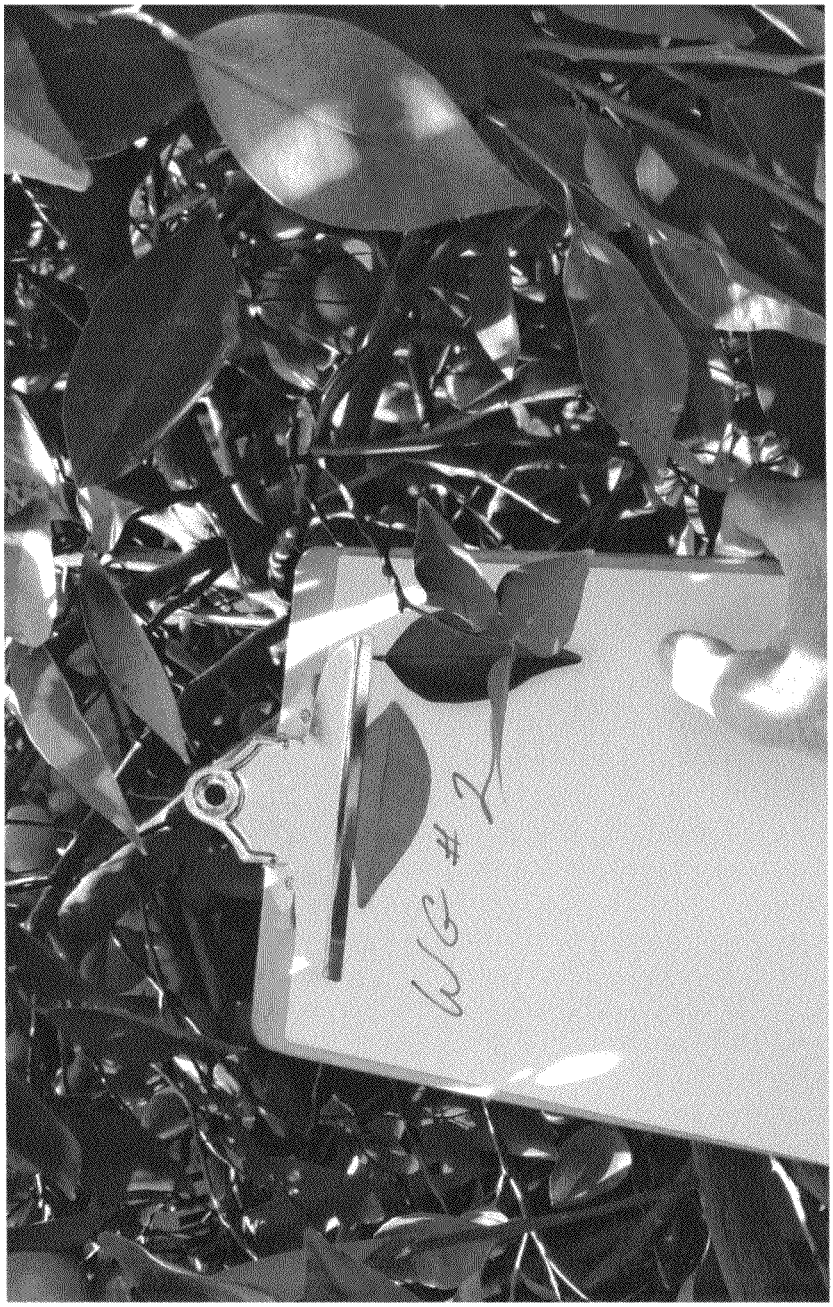

Latin name of the genus and species: *Citrus reticulata.*
Variety denomination: 'WG 02'.

BACKGROUND OF THE INVENTION

The new cultivar is a product of a planned crossing program in January of 2000 under the direction of the inventor, Bill Roe, a citizen of The United States. The seed parent is unpatented variety *Citrus reticulata* 'Darcy'. The pollen parent is the unpatented variety *Citrus reticulata* 'Honey'.

This new variety was found in November of 2006 in a commercial nursery in Winter Haven, Fla. Plants were first propagated by tissue culture in 2006 and subsequently grafted onto rootstocks US-897 and US-942. Development, evaluation, tissue culture and grafting all first took place at the inventor's commercial nursery in Winter Haven, Fla. U.S.A. Subsequent evaluations of the variety have shown the characteristics to be true to type.

SUMMARY OF THE INVENTION

The cultivar 'WG 02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WG 02' These characteristics in combination distinguish 'WG 02' as a new and distinct *Citrus reticulata* cultivar:

1. Peels easily and dry.
2. Typical oblate tangerine appearance.
3. Very low seed count, average less that 2 per fruit.
4. Maintains moderately high acid levels.
5. Ripens November through December.

COMPARISON TO PARENT VARIETIES

Plants of the new cultivar 'WG 02' are similar to plants of the seed parent; unpatented variety *Citrus reticulata* 'Dancy' in most horticultural characteristics, including the need for cross pollination, however, plants of the new cultivar 'WG 02' produces an oblate shaped fruit with a non-oily, easily peeled rind, that does not puff as badly as seed parent 'Dancy'. Additionally, 'WG 02' also produces fruit that tends to hold acid level well and does not have internal dryness issues compared to seed parent 'Dancy'.

Plants of the new cultivar 'WG 02' are similar to plants of the pollen parent; unpatented variety *Citrus reticulata* 'Honey ' in most horticultural characteristics, however, plants of the new cultivar 'WG 02' produces fruit with less seed and a higher orange peel color as well as lower in sugar level than pollen parent 'Honey'. Additionally, 'WG 02' also produces fruit earlier and the fruit is more perishable than pollen parent 'Honey'.

COMMERCIAL COMPARISON

The new variety is best compared to the commercial variety, *Citrus reticulata* 'Sunburst Tang', unpatented. 'WG 02' is similar to 'Sunburst Tang' in many horticultural characteristics however, 'WG 02' produces fruit that is much easier to peel as well as with much fewer seeds. Additionally, the new variety 'WG 02' produces fruit of a more oblate shape with a smoother peel texture and a lower external orange color till overripe compared to 'Sunburst Tang'.

'WG 02' can also be compared to *Citrus reticulata* 'Lee Citrus', unpatented. The two varieties are similar in many horticultural characteristics, however 'WG 02' produces less seedy fruit of more oblate form that is easier to peel and producing less oil when peeled compared to 'Lee Citrus'. In addition 'WG 02' produces a tree that grows less upright than 'Lee Citrus'.

BRIEF DESCRIPTION OF THE PHOTOGRAPHS

The accompanying photograph in FIG. 1 illustrates in full color examples of typical fruit harvested from 'WG 02'.

Figure 2:
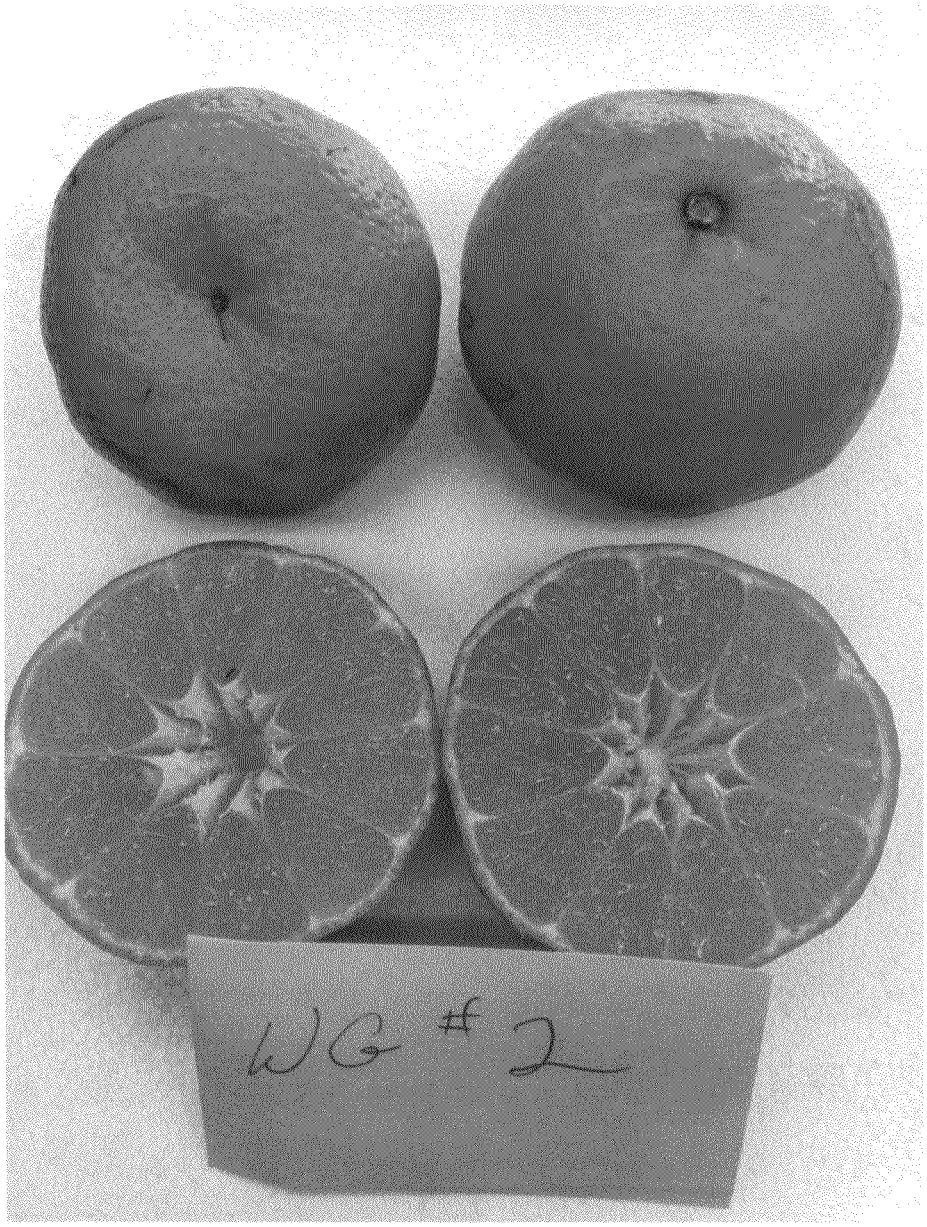

FIG. 2 illustrates in full color typical foliage of 'WG 02'.

Photographs are taken of plants approximately 3 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'WG 02' plants grown outdoors under commercial trial conditions in Winter Haven, Fla. U.S.A. The growing temperature ranged from 10° C. to 35° C. during the day and −4° C. to 20° C. at night. Measurements and numerical values represent an average from the most typical specimens.

Botanical classification: *Citrus reticulata* 'WG 02'.

PROPAGATION

'WO 02' is typically grafted onto rootstock of *Citrus reticulata* US-897 and US-942.

PLANT

Age of the plant described: Approximately 3 years.

Canopy density: Tree tends to spread as opposed to growing upright. Limbs easily weep under heavy fruit load. Fruiting occurs throughout the canopy and causes an opening up of the interior of the tree under heavy crop load.

Height: N/A.

Growth rate: Approximately 3 years to 200 cm.

Vigor: Vigorous Spring flush with crop set heavy enough to cause limb breakage.

Length of primary lateral branches: Approximately 52-60 cm. prior to splitting.

Quantity of lateral branches: 7-9.

Angle of lateral branches from main trunk: 60°+/− from Horizontal (150°+/−).

Branching characteristics: Limber branched that are not prone to splitting at trunk.

Branching arrangement: Prolific Branching and weeps heavily under fruit loading.

Branch diameter: Average 1.5-3.0 cm.

Trunk texture: Smooth.

Trunk color: Near RHS Grey-Brown 199B.

Trunk diameter: Average 7.5-8 cm on a 3 year old plant.

FOLIAGE

Leaf:

*Average length.*—7-11.5 cm. Average of 9-9.25 cm.

*Average width.*—3.5-6 cm. Average of 4.5 cm.

*Arrangement.*—Alternate.

*Shape of blade.*—Typical.

*Apex.*—Last cm. of leaf tip is generally less than 1 cm wide.

*Base.*—Very thin pedicule, almost like a short stem.

*Attachment.*—1 cm.+/−, very thin.

*Margin.*—Smooth to very light notching.

*Texture of top surface.*—Smooth.

*Texture of under side.*—Smooth.

*Color.*—Mature foliage upper side: Near RHS Green 139A. Mature foliage under side: Near RHS Green 141B.

*Petiole.*—Length: Average length 1-1.5 cm. Average of 1.25 cm. Pubescence: None. Color: Upper and lower surfaces near Yellow-Green 144B.

FLOWER

Plants in full bloom approximately on March 22.

FRUIT

General shape: Oblate.

Median cross section: 6.83 cm.

Flesh color when ripe: Near RHS Orange-Red N30B.

Brix at consumption: 9.6 Nov. 16, 2011.

Brix at harvest: 9.6. Acid 0.83 Ratio of 11.56.

Average weight: 145 grams.

Minimum weight: 110 grams.

Maximum weight: 180 grams.

Height: 5.02-5.32 cm.

Width: 6.66-6.96 cm.

Segment number per fruit: 9-10.

Fruit peduncle length: 0.6-2.6 cm. Average of 1.2.

Fruit peduncle width: 55-80 mm. Average of 60 mm.

Skin color at harvest: Near RHS Orange-Red 33B.

Skin/rind thickness: Fairly thin: 2-3 cm.

Skin adherence to flesh at maturity: Peels clean, start somewhat in pieces, but finishes easily.

Skin/rind texture: Fairly smooth.

Base necked: No.

Harvest time:

*First harvest.*—November.

*Last harvest.*—December.

Overall cropping quantity: Fruits heavily with cross pollination.

Mature seed color: Near RHS White 155A.

Quantity seed per fruit: Less than 2 per fruit.

Seed shape: Elliptical.

Seed length: 1 cm.

Seed width: 0.5 cm.

Other: Seeds typically aborted.

OTHER CHARACTERISTICS

Storage life: Storage life is a minimum of 14 days at 2° C.

Disease/pest resistance: Neither resistance nor susceptibility to the normal diseases and pests of *Citrus reticulata* has been observed.

Temperature tolerance: Normal tolerance for cold temperatures, similar to commercial varieties of *Citrus reticulata.*

What is claimed is:

1. A new and distinct cultivar of *Citrus reticulata* plant named 'WG 02' as herein illustrated and described.

* * * * *